(12) United States Patent
Williamson et al.

(10) Patent No.: US 10,219,725 B2
(45) Date of Patent: Mar. 5, 2019

(54) PATIENT MOBILITY SURFACE ASSESSMENT SYSTEM AND METHOD

(71) Applicant: Hill-Rom Services, Inc., Batesville, IN (US)

(72) Inventors: Rachel L. Williamson, Batesville, IN (US); Robert M. Zerhusen, Cincinatti, OH (US); Charles A. Lachenbruch, Lakeway, TX (US); Timothy J. Receveur, Guilford, IN (US); Nicholas C. Batta, Batesville, IN (US); Yaoning Wu, Terre Haute, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 112 days.

(21) Appl. No.: 13/788,665

(22) Filed: Mar. 7, 2013

(65) Prior Publication Data

US 2014/0066815 A1    Mar. 6, 2014

Related U.S. Application Data

(60) Provisional application No. 61/696,750, filed on Sep. 4, 2012.

(51) Int. Cl.
*A61B 5/11* (2006.01)
*A61B 5/00* (2006.01)
(Continued)

(52) U.S. Cl.
CPC .............. *A61B 5/11* (2013.01); *A61B 5/1118* (2013.01); *A61B 5/6892* (2013.01);
(Continued)

(58) Field of Classification Search
CPC ........................................................ A61B 5/11
(Continued)

(56) References Cited

U.S. PATENT DOCUMENTS 4,114,188 A * 9/1978 Carter ................. A61B 5/4356
600/561
9,295,600 B2 * 3/2016 Receveur .............. A61B 5/1118
(Continued)

FOREIGN PATENT DOCUMENTS

EP       2 508 128 A1    4/2010
WO    2010/039255 A2    4/2010

OTHER PUBLICATIONS

Yousefi et al., "A Smart Bed Platform for Monitoring & Ulcer Prevention", 2011 4th International Conference on Biomedical Engineering and Informatics (BMEI), Oct. 15, 2011.
(Continued)

*Primary Examiner* — Rene Towa
*Assistant Examiner* — H. Q. Nguyen
(74) *Attorney, Agent, or Firm* — Barnes & Thornburg LLP

(57) ABSTRACT

A patient support apparatus includes a control system that measures changes in the pressure of one or more zones of a patient supporting surface and utilizes the changes in pressure to determine the mobility of a person supported on the patient supporting surface. The mobility of the person may be measured using one of several methods. The mobility measurement results in the determination of a mobility score. The mobility score is graphically displayed on a user interface that is interactive and allows a user to view additional information besides the mobility score.

20 Claims, 8 Drawing Sheets

(51) Int. Cl.
  *A61G 7/05* (2006.01)
  *A61G 7/057* (2006.01)
  *A61G 7/015* (2006.01)
  *A61B 5/044* (2006.01)

(52) U.S. Cl.
  CPC .......... *A61G 7/0513* (2016.11); *A61G 7/0524* (2016.11); *A61B 5/044* (2013.01); *A61B 5/7242* (2013.01); *A61B 5/742* (2013.01); *A61B 2562/0247* (2013.01); *A61B 2562/043* (2013.01); *A61G 7/015* (2013.01); *A61G 7/0573* (2013.01); *A61G 7/05776* (2013.01); *A61G 2203/12* (2013.01); *A61G 2203/20* (2013.01); *A61G 2203/34* (2013.01); *A61G 2203/44* (2013.01)

(58) Field of Classification Search
  USPC ........................................................ 600/595
  See application file for complete search history.

(56) References Cited

U.S. PATENT DOCUMENTS

| | | |
|---|---|---|
| 2005/0240121 A1* | 10/2005 | Ferriss ................. A61B 5/1116 600/587 |
| 2006/0075559 A1 | 4/2006 | Skinner et al. |
| 2009/0070939 A1* | 3/2009 | Hann ....................... A61B 5/11 5/652.1 |
| 2011/0302719 A1 | 12/2011 | Schwirian et al. |
| 2013/0218053 A1* | 8/2013 | Kaiser .................. A61B 5/1123 600/595 |
| 2014/0024971 A1* | 1/2014 | Bunn ....................... A61B 5/11 600/595 |

OTHER PUBLICATIONS

European search report from related EP 13 18 2687 dated Nov. 18, 2013, 9 pages.

\* cited by examiner

PATIENT MOBILITY SURFACE ASSESSMENT SYSTEM AND METHOD

CROSS-REFERENCE TO RELATED APPLICATIONS

This application claims priority under 35 U.S.C. § 119(e) to U.S. Provisional Application Ser. No. 61/696,750, filed Sep. 4, 2012, which is expressly incorporated by reference herein.

BACKGROUND

The present disclosure is related to patient support apparatuses that monitor patient conditions. More specifically, the present disclosure is related to a patient support apparatus that includes a control system that monitors movement of a patient supported on a patient supporting surface and displays information related to the movement on a user interface.

The mobility of a person supported on a patient support apparatus is of interest to caregivers in assessing the risk of the patient developing skin injuries, such as pressure sores, for example. Generally, mobility is scored subjectively by caregivers. Many factors introduce error into the mobility scoring process.

SUMMARY

The present application discloses one or more of the features recited in the appended claims and/or the following features which, alone or in any combination, may comprise patentable subject matter:

A patient support apparatus comprises a patient supporting surface, a plurality of pressure sensors, a user interface, and a controller. The patient support surface includes a number of bladders organized into a plurality of zones. Each pressure sensor measures a pressure in a respective zone. The user interface includes a display and a number of user inputs. The controller is in communication with the pressure sensors to receive data signals indicative of the pressure in each of the zones. The controller processes the data signals from the pressure sensors to determine a measure of mobility of a patient supported on the patient supporting surface.

In some embodiments, the controller is in communication with the user interface and operable to cause the user interface to display the measure of mobility of the patient.

In some embodiments, the measure of mobility of the patient is stored over time to create a data array. In some embodiments, the measure of mobility is displayed graphically over time. In some embodiments, the mobility of a patient supported on the patient supporting surface is determined by integrating the differences between an actual pressure measured and a nominal pressure over a predetermined period. In some embodiments, the mobility of the patient is determined by determining a mobility index for each of the plurality of zones and summing each of the mobility indices to arrive at a mobility score. In some embodiments, each of the mobility indices is modified by at least one predetermined factor. In some embodiments, the at least one predetermined factor includes at least one of a patient factor, a bed factor, and a statistical scaling factor.

In some embodiments, the mobility of a patient supported on the patient supporting surface is determined by evaluating the coefficient of variation of a number of pressure samples over a predetermined period. In some embodiments, the mobility of the patient is determined by determining a mobility index for each of the plurality of zones and summing each of the mobility indices to arrive at a mobility score In some embodiments, each of the mobility indices is modified by at least one predetermined factor. In some embodiments, the at least one predetermined factor includes at least one of a patient factor, a bed factor, and a statistical scaling factor.

In some embodiments, the mobility of a patient supported on the patient supporting surface is determined by calculating the work transferred from the person supported on the patient supporting surface to the patient supporting surface. In some embodiments, the mobility of the patient is determined by determining a mobility index for each of the plurality of zones and summing each of the mobility indices to arrive at a mobility score. In some embodiments, each of the mobility indices is modified by at least one predetermined factor. In some embodiments, the at least one predetermined factor includes at least one of a patient factor, a bed factor, and a statistical scaling factor. In some embodiments, the measure of mobility over time includes a number of data points. In some embodiments, each of the data points may be activated to display additional information. In some embodiments, the additional information includes a summary of data accumulated to the point in time corresponding with the data point. In some embodiments, additional information regarding patient mobility is displayed on the display. In some embodiments, the additional information includes a graphical indication of the time at which the person made a significant movement on the patient supporting surface.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
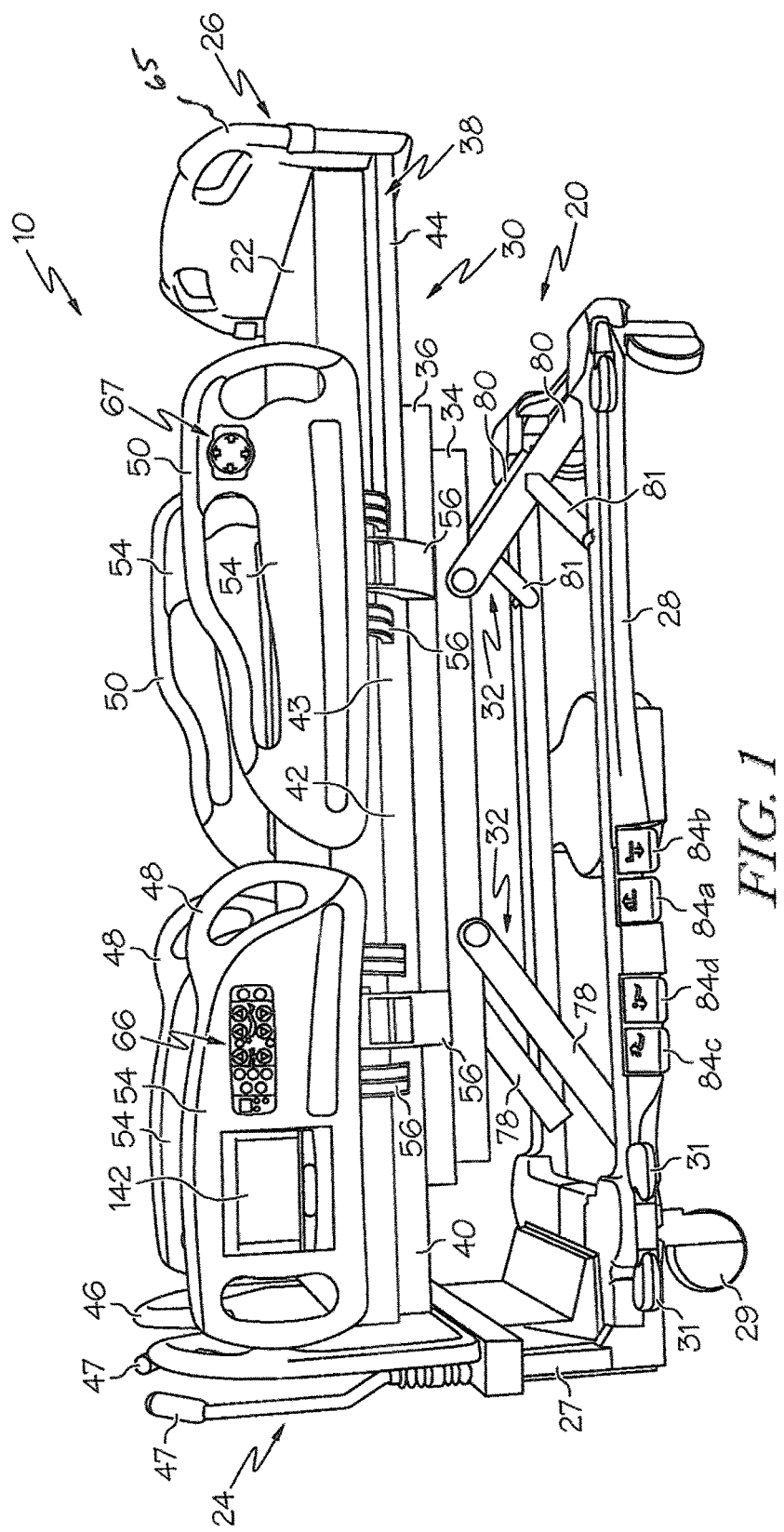
FIG. 1 is a perspective view of a patient support apparatus including a user interface and a control system for measuring the mobility of a person supported on the patient support apparatus.

A patient support apparatus, such as illustrative hospital bed 10, includes a patient support structure such as a frame 20 that supports a surface or mattress 22 as shown in FIG. 1. Thus, according to this disclosure a bed frame, a mattress or both are examples of things considered to be within the scope of the term "patient support structure." However, this disclosure is applicable to other types of patient support apparatuses and other patient support structures, including other types of beds, surgical tables, examination tables, stretchers, and the like. As will be described below in connection with FIGS. 3 and 4, bed 10 includes a patient mobility tracking system to track and display data indicative of the mobility of a patient supported on the bed 10.

Referring again to FIG. 1, frame 20 of bed 10 includes a base 28, an upper frame assembly 30 and a lift system 32 coupling upper frame assembly 30 to base 28. Lift system 32 is operable to raise, lower, and tilt upper frame assembly 30 relative to base 28. Bed 10 has a head end 24 and a foot end 26. Hospital bed 10 further includes a footboard 65 at the foot end 26 and a headboard 46 at the head end 24. Illustrative bed 10 includes a pair of push handles 47 coupled to an upstanding portion 27 of base 28 at the head end 24 of bed 10. Headboard 46 is coupled to upstanding portion 27 of base 28 as well. Footboard 65 is coupled to upper frame assembly 30. Base 28 includes wheels or casters 29 that roll along a floor (not shown) as bed 10 is moved from one location to another. A set of foot pedals 31 are coupled to base 28 and are used to brake and release casters 29.

Illustrative hospital bed 10 has four siderail assemblies coupled to upper frame assembly 30 as shown in FIG. 1. The four siderail assemblies include a pair of head siderail assemblies 48 (sometimes referred to as head rails) and a pair of foot siderail assemblies 50 (sometimes referred to as foot rails). Each of the siderail assemblies 48, 50 is movable between a raised position, as shown in FIG. 1, and a lowered position (not shown). Siderail assemblies 48, 50 are sometimes referred to herein as siderails 48, 50. Each siderail 48, 50 includes a barrier panel 54 and a linkage 56. Each linkage 56 is coupled to the upper frame assembly 30 and is configured to guide the barrier panel 54 during movement of siderails 48, 50 between the respective raised and lowered positions. Barrier panel 54 is maintained by the linkage 56 in a substantially vertical orientation during movement of siderails 48, 50 between the respective raised and lowered positions.

Upper frame assembly 30 includes a lift frame 34, a weigh frame 36 supported with respect to lift frame 34, and a patient support deck 38. Patient support deck 38 is carried by weigh frame 36 and engages a bottom surface of surface 22. Patient support deck 38 includes a head section 40, a seat section 42, a thigh section 43 and a foot section 44 in the illustrative example as shown in FIG. 1 and as shown diagrammatically in FIG. 2. Sections 40, 43, 44 are each movable relative to weigh frame 36. For example, head section 40 pivotably raises and lowers relative to seat section 42 whereas foot section 44 pivotably raises and lowers relative to thigh section 43. Additionally, thigh section 43 articulates relative to seat section 42. Also, in some embodiments, foot section 44 is extendable and retractable to change the overall length of foot section 44 and therefore, to change the overall length of deck 38. For example, foot section 44 includes a main portion 45 and an extension 47 in some embodiments as shown diagrammatically in FIG. 2.

In the illustrative embodiment, seat section 42 is fixed in position with respect to weigh frame 36 as patient support deck 38 moves between its various patient supporting positions including a horizontal position, shown in FIG. 1, to support the patient in a supine position, for example, and a chair position (not shown) to support the patient in a sitting up position. In other embodiments, seat section 42 also moves relative to weigh frame 36, such as by pivoting and/or translating. Of course, in those embodiments in which seat section 42 translates along upper frame 30, the thigh and foot sections 43, 44 also translate along with seat section 42. As bed 10 moves from the bed position to the chair position, foot section 44 lowers relative to thigh section 43 and shortens in length due to retraction of the extension 47 relative to main portion 45. As bed 10 moves from the chair position to the bed position, foot section 44 raises relative to thigh section 43 and increases in length due to extension of the extension relative to main portion 45. Thus, in the chair position, head section 40 extends upwardly from weigh frame 36 and foot section extends downwardly from thigh section 43.

Figure 2:
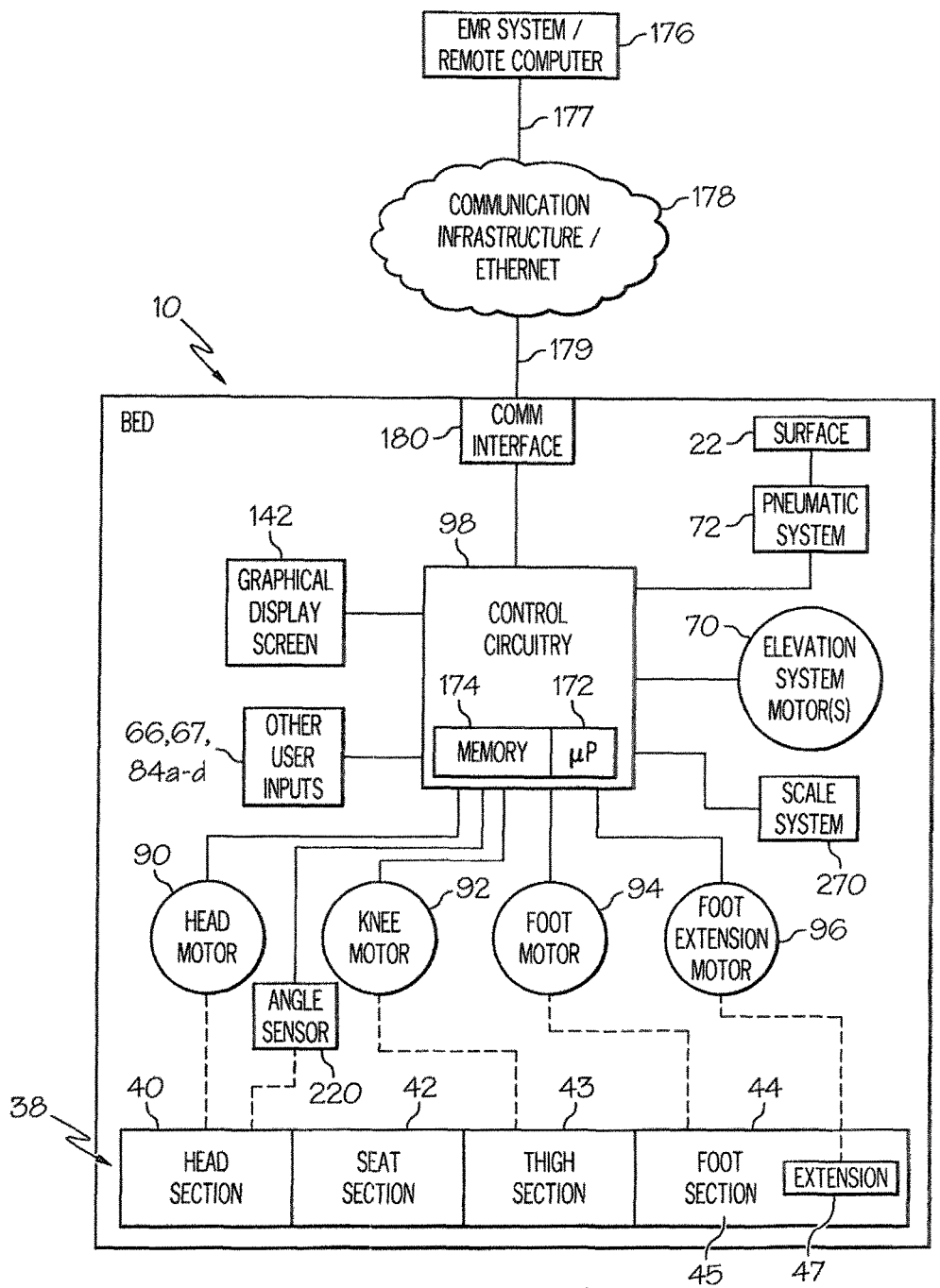
FIG. 2 is a block diagram of the patient support apparatus of FIG. 1.

As shown diagrammatically in FIG. 2, bed 10 includes a head motor or actuator 90 coupled to head section 40, a knee motor or actuator 92 coupled to thigh section 43, a foot motor or actuator 94 coupled to foot section 44, and a foot extension motor or actuator 96 coupled to foot extension 47. Actuators 90, 92, 94, 96 may include, for example, an electric motor of a linear actuator. In those embodiments in which seat section 42 translates along upper frame 30 as mentioned above, a seat motor or actuator (not shown) is also provided. Head actuator 90 is operable to raise and lower head section 40, knee actuator 92 is operable to articulate thigh section 43 relative to seat section 42, foot actuator 94 is operable to raise and lower foot section 44 relative to thigh section 43, and foot extension actuator 96 is operable to extend and retract extension 47 of foot section 44 relative to main portion 45 of foot section 44.

In some embodiments, bed 10 includes a pneumatic system 72 that controls inflation and deflation of various air bladders or cells (some of which are shown diagrammatically in FIG. 3) of surface 22. The pneumatic system 72 is represented in FIG. 2 as a single block but that block 72 is intended to represent one or more air sources (e.g., a fan, a blower, a compressor) and associated valves, manifolds, air passages, air lines or tubes, pressure sensors, and the like, as well as the associated electric circuitry, that are typically included in a pneumatic system for inflating and deflating air bladders of mattresses of hospital beds.

As also shown diagrammatically in FIG. 2, lift system 32 of bed 10 includes one or more elevation system motors or actuators 70, which in some embodiments, comprise linear actuators with electric motors. Thus, actuators 70 are sometimes referred to herein as actuators 70. Alternative actuators or motors contemplated by this disclosure include hydraulic cylinders and pneumatic cylinders, for example. The actuators 70 of lift system 32 are operable to raise, lower, and tilt upper frame assembly 30 relative to base 28. In the illustrative embodiment, one of actuators 70 is coupled to, and acts upon, a set of head end lift arms 78 and another of actuators 70 is coupled to, and acts upon, a set of foot end lift arms 80 to accomplish the raising, lowering and tilting functions of upper frame 30 relative to base 28. Guide links 81 are coupled to base 28 and to lift arms 80 in the illustrative example as shown in FIG. 1. Lift system of bed 10 is substantially similar to the lift system of the VERSA-CARE® bed available from Hill-Rom Company, Inc. Other aspects of bed 10 are also substantially similar to the VERSACARE® bed and are described in more detail in U.S. Pat. Nos. 6,658,680; 6,611,979; 6,691,346; 6,957,461; and 7,296,312, each of which is hereby expressly incorporated by reference herein.

In the illustrative example, bed 10 has four foot pedals 84a, 84b, 84c, 84d coupled to base 28 as shown in FIG. 1. Foot pedal 84a is used to raise upper frame assembly 30 relative to base 28, foot pedal 84b is used to lower frame assembly 30 relative to base 28, foot pedal 84c is used to raise head section 40 relative to frame 36, and foot pedal 84d is used to lower head section 40 relative to frame 36. In other embodiments, foot pedals 84a-d are omitted.

Each siderail 48 includes a first user control panel 66 coupled to the outward side of the associated barrier panel 54 and each siderail 50 includes a second user control panel 67 coupled to the outward side of the associated barrier panel 54. Controls panels 66, 67 include various buttons that are used by a caregiver (not shown) to control associated functions of bed 10. For example, control panel 66 includes buttons that are used to operate head actuator 90 to raise and lower the head section 40, buttons that are used to operate knee actuator to raise and lower the thigh section, and buttons that are used to operate actuators 70 to raise, lower, and tilt upper frame assembly 30 relative to base 28. In the illustrative embodiment, control panel 67 includes buttons that are used to operate actuator 94 to raise and lower foot section 44 and buttons that are used to operate actuator 96 to extend and retract foot extension 47 relative to main portion 45. In some embodiments, the buttons of control panels 66, 67 comprise membrane switches.

As shown diagrammatically in FIG. 2, bed 10 includes control circuitry 98 that is electrically coupled to actuators 90, 92, 94, 96 and to actuators 70 of lift system 32. Control circuitry 98 is represented diagrammatically as a single block 98 in FIG. 6, but control circuitry 98 in some embodiments comprises various circuit boards, electronics modules, and the like that are electrically and communicatively interconnected. Control circuitry 98 includes one or more microprocessors 172 or microcontrollers that execute software to perform the various control functions and algorithms described herein. Thus, circuitry 98 also includes memory 174 for storing software, variables, calculated values, and the like as is well known in the art.

As also shown diagrammatically in FIG. 2, a user inputs block represents the various user inputs such as buttons of control panels 66, 67 and pedals 84a-d, for example, that are used by the caregiver or patient to communicate input signals to control circuitry 98 of bed 10 to command the operation of the various actuators 70, 90, 92, 94, 96 of bed 10, as well as commanding the operation of other functions of bed 10. Bed 10 includes at least one graphical user input or display screen 142 coupled to a respective siderail 48 as shown in FIG. 1. Display screen 142 is coupled to control circuitry 98 as shown diagrammatically in FIG. 2. In some embodiments, two graphical user interfaces 142 are provided and are coupled to respective siderails 48. Alternatively or additionally, one or more graphical user interfaces are coupled to siderails 50 and/or to one or both of the headboard 46 and footboard 65. Thus, it is contemplated by this disclosure that a graphical user interface 142 may be coupled to any of barriers 65, 46, 48, 50 of bed 10. Alternatively or additionally, graphical user interface 142 is provided on a hand-held device such as a pod or pendant that communicates via a wired or wireless connection with control circuitry 98.

Control circuitry 98 receives user input commands from graphical display screen 142 when display screen 142 is activated. The user input commands control various functions of bed 10 such as controlling the pneumatic system 72 and therefore, the surface functions of surface 22. In some embodiments, the input commands entered on user interface 142 also control the functions of one or more of actuators 70, 90, 92, 94, 96 but this need not be the case. In some embodiments, input commands entered on the user interface 142 also control functions of a scale system 270, which is discussed in more detail below.

Various examples of the various alternative or additional functions of bed 10 that are controlled by display screen 142 in various embodiments can be found in U.S. Patent Application Publication Nos. 2008/0235872 A1 and 2008/0172789 A1 and in U.S. application Ser. No. 13/249,336, filed Sep. 30, 2011, and titled "Hospital Bed with Graphical User Interface Having Advanced Functionality," each of which is hereby incorporated by reference herein. According to this disclosure, control circuitry 98 is configured to deactivate display screen 142 if screen 142 has not been used to control a function of bed 10 within a threshold amount of time, such as 30 seconds to 5 minutes, for example. Once display screen 142 has been deactivated, inadvertent or accidental activation of display screen 142, as well as inadvertent or accidental activation of functions of bed 10 via use of display screen 142, is prevented because a user is required to perform a certain touch and swipe sequence on display screen 142 to re-activate it as is discussed below in connection with FIGS. 3 and 4.

In some embodiments, control circuitry 98 of bed 10 communicates with a remote computer device 176 via communication infrastructure 178 such as an Ethernet of a healthcare facility in which bed 10 is located and via communications links 177, 179 as shown diagrammatically in FIG. 2. Computer device 176 is sometimes simply referred to as a "computer" herein. Remote computer 176 may be part of an electronic medical records (EMR) system, for example. However, it is within the scope of this disclosure for circuitry 98 of bed 10 to communicate with other computers such as those included as part of a nurse call system, a physician ordering system, an admission/discharge/transfer (ADT) system, or some other system used in a healthcare facility in other embodiments. Ethernet 178 in FIG. 2 is illustrated diagrammatically and is intended to represent all of the hardware and software that comprises a network of a healthcare facility.

In the illustrative embodiment, bed 10 has a communication interface or port 180 which provides bidirectional communication via link 179 with infrastructure 178 which, in turn, communicates bidirectionally with computer 176 via link 177. Link 179 is a wired communication link in some embodiments and is a wireless communications link in other embodiments. Thus, communications link 179, in some embodiments, comprises a cable that connects bed 10 to a wall mounted jack that is included as part of a bed interface unit (BIU) or a network interface unit (NIU) of the type shown and described in U.S. Pat. Nos. 7,538,659 and 7,319,386 and in U.S. Patent Application Publication Nos. 2009/0217080 A1, 2009/0212925 A1 and 2009/0212926 A1, each of which are hereby expressly incorporated by reference herein. In other embodiments, communications link 179 comprises wireless signals sent between bed 10 and a wireless interface unit of the type shown and described in U.S. Patent Application Publication No. 2007/0210917 A1 which is hereby expressly incorporated by reference herein. Communications link 177 comprises one or more wired links and/or wireless links as well, according to this disclosure.

Figure 3:
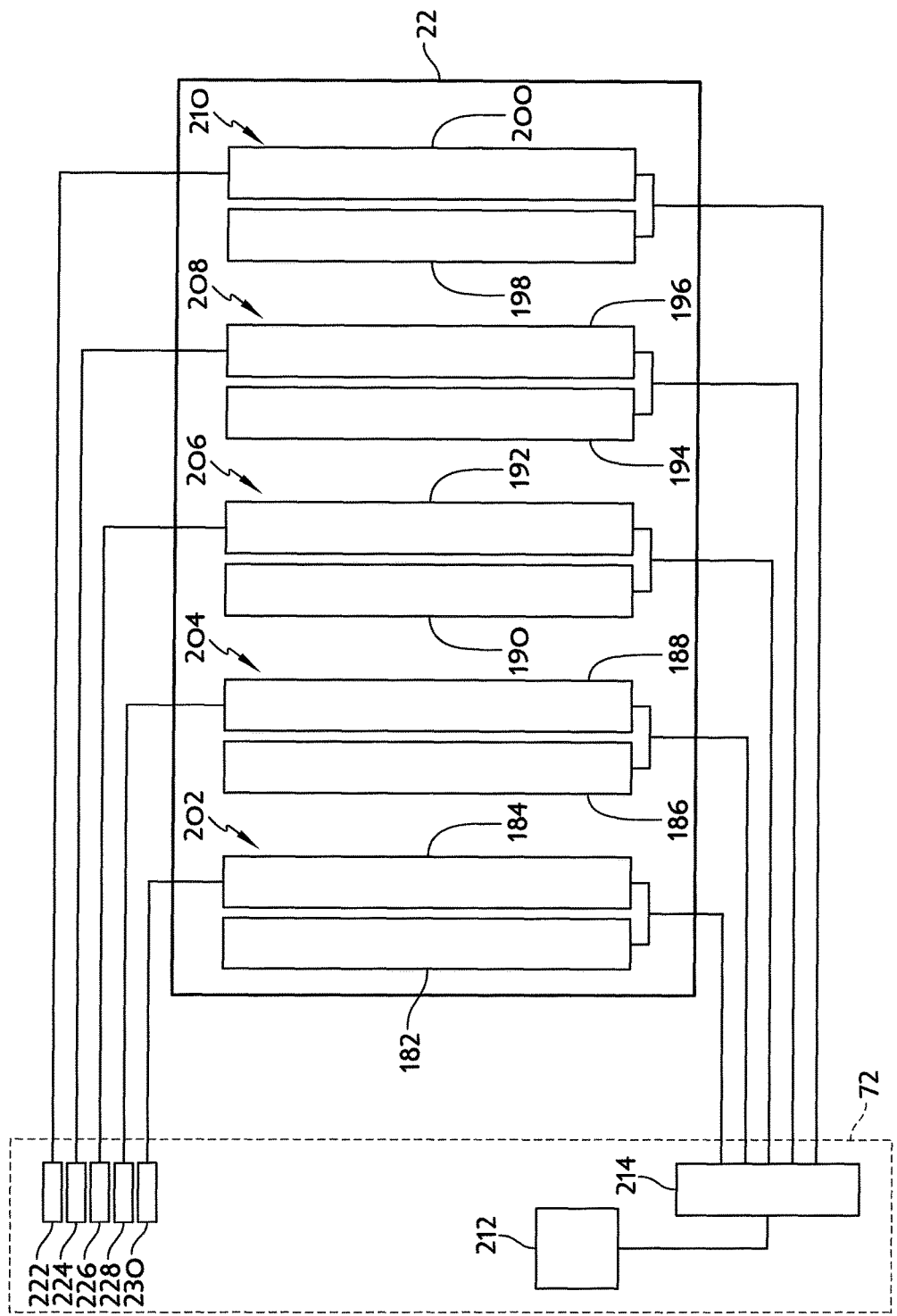
FIG. 3 is a partial block diagram of a portion of a support surface and pneumatic system of the patient support apparatus of FIG. 1.

In one illustrative embodiment, the surface 22 includes a number of bladders 182, 184, 186, 188, 190, 192, 194, 196, 198, and 200 as shown in FIG. 3. The bladders 182, 184, 186, 188, 190, 192, 194, 196, 198, and 200 are grouped into five zones 202, 204, 206, 208, and 210 with two bladders in each zone 202, 204, 206, 208, and 210, the bladders for each zone 202, 204, 206, 208, and 210 being in fluid communication with a free flow of air between the bladders. For example, zone 202 includes bladders 182 and 184 connected together and in fluid communication. The pneumatic system 72 includes a source of pressurized air 212 and a manifold 214 that directs air to and from each of the zones 202, 204, 206, 208, and 210. In addition, the pneumatic system 72 includes pressure sensors 222, 224, 226, 228, and 230 that are each in fluid communication with a respective zone 202, 204, 206, 208, and 210 and operable to measure a pressure in the respective zone.

The control circuitry 98 is operable to receive a signal indicative of the pressure in each of the zones 202, 204, 206, 208, and 210 from the respective pressure sensors 222, 224, 226, 228, and 230 on a regular basis, such as once every 30 milliseconds, for example. The pressure signal from each sensor 222, 224, 226, 228, and 230 is collected in an array. A generalization of the array of pressure measurements is shown in Table 1 below.

TABLE 1

| Zone | Time 1 | Time 2 | Time 3 | Time 4 | Time 5 | Time n − 1 | Time n |
|---|---|---|---|---|---|---|---|
| 202 | $P(202)_{t1}$ | $P(202)_{t2}$ | $P(202)_{t3}$ | $P(202)_{t4}$ | $P(202)_{t5}$ | $P(202)_{m-1}$ | $P(202)_m$ |
| 204 | $P(204)_{t1}$ | $P(204)_{t2}$ | $P(204)_{t3}$ | $P(204)_{t4}$ | $P(204)_{t5}$ | $P(204)_{m-1}$ | $P(204)_m$ |
| 206 | $P(206)_{t1}$ | $P(206)_{t2}$ | $P(206)_{t3}$ | $P(206)_{t4}$ | $P(206)_{t5}$ | $P(206)_{m-1}$ | $P(206)_m$ |
| 208 | $P(208)_{t1}$ | $P(208)_{t2}$ | $P(208)_{t3}$ | $P(208)_{t4}$ | $P(208)_{t5}$ | $P(208)_{m-1}$ | $P(208)_m$ |
| 210 | $P(210)_{t1}$ | $P(210)_{t2}$ | $P(210)_{t3}$ | $P(210)_{t4}$ | $P(210)_{t5}$ | $P(210)_{m-1}$ | $P(210)_m$ |

The change in pressure in each zone is then calculated and stored in a second array. For example, the difference in pressure in zone 202 between Time 1 and Time 2 is calculated by calculating the difference $\Delta P(202)_{t2-1} = P(202)_{t2} - P(202)_{t1}$. A generalization of the pressure differences is shown in Table 2 below.

TABLE 2

| Zone | $\Delta P_{t2-1}$ | $\Delta P_{t3-2}$ | $\Delta P_{t4-3}$ | $\Delta P_{t5-4}$ | $\Delta P_{t(n-1)-5}$ | $\Delta P_{m-(n-1)}$ |
|---|---|---|---|---|---|---|
| 202 | $\Delta P(202)_{t2-1}$ | $\Delta P(202)_{t3-2}$ | $\Delta P(202)_{t4-3}$ | $\Delta P(202)_{t5-4}$ | $\Delta P(202)_{t(n-1)-5}$ | $\Delta P(202)_{m-(n-1)}$ |
| 204 | $\Delta P(204)_{t2-1}$ | $\Delta P(204)_{t3-2}$ | $\Delta P(204)_{t4-3}$ | $\Delta P(204)_{t5-4}$ | $\Delta P(204)_{t(n-1)-5}$ | $\Delta P(204)_{m-(n-1)}$ |
| 206 | $\Delta P(206)_{t2-1}$ | $\Delta P(206)_{t3-2}$ | $\Delta P(206)_{t4-3}$ | $\Delta P(206)_{t5-4}$ | $\Delta P(206)_{t(n-1)-5}$ | $\Delta P(206)_{m-(n-1)}$ |
| 208 | $\Delta P(208)_{t2-1}$ | $\Delta P(208)_{t3-2}$ | $\Delta P(208)_{t4-3}$ | $\Delta P(208)_{t5-4}$ | $\Delta P(208)_{t(n-1)-5}$ | $\Delta P(208)_{m-(n-1)}$ |
| 210 | $\Delta P(210)_{t2-1}$ | $\Delta P(210)_{t3-2}$ | $\Delta P(210)_{t4-3}$ | $\Delta P(210)_{t5-4}$ | $\Delta P(210)_{t(n-1)-5}$ | $\Delta P(210)_{m-(n-1)}$ |

The control circuitry 98 will then compare every two pressure differences in a particular zone with a pre-determined threshold to determine if the difference is less than the threshold. If the difference is less than the pre-determined threshold, then the two consecutive pressure measurements in the pressure array of Table 1 are reset to the average between the two. This process is repeated for each pressure difference in Table 2 so that the pressure measurements stored in Table 1 are progressively filtered. If the difference is greater than the threshold, then the pressures in the pressure array of Table 1 are maintained at the measured values.

If the surface 22 is constructed such that a substantial portion of the weight of a person is supported on the bladders 182, 184, 186, 188, 190, 192, 194, 196, 198, and 200, the movement of the person may be measured by changes in the pressure in the bladders 182, 184, 186, 188, 190, 192, 194, 196, 198, and 200. In one approach, the movement of a person relative to a single zone may be calculated by integrating the changes in pressure over time using the integration model shown in Equation 1 below.

$$MobilityIndex_{Zone} = \int_{t}^{t+N} (P_t - P_0)\, dt \qquad (1)$$

where N is the number of samples in a defined time window, $P_t$ is the pressure at time t, and $P_0$ is the pressure with no movement as determined from an initial condition or a long running average. With this approach, the MobilityIndex is a relative value for a particular time window and will give an indication of the amount of movement taking place on a particular zone. Each mobility index for each time period is stored in an including each of the different zones in the same time window. As will be discussed in further detail, the MobilityIndex for each of the zones and time windows may be used to make assessments of the person supported on the surface 22.

In another approach, the relative movement of a person can be measured by determining a coefficient of variation of the samples in a time window. The coefficient of variation is calculated using each pressure measurement in the pressure array over a given time period to determine a standard deviation and mean for the sample and using these values to calculate the coefficient of variation as shown in Equation 2.

$$MobilityIndex_{Zone} = \frac{StdDev}{Mean} \qquad (2)$$

where the coefficient of variation for the particular zone may be compared or accumulated with the coefficient of variation for other zones to determine a mobility index of a person supported on the surface 22.

In still another approach, the mobility index of a person on the surface 22 may be calculated by determining the work done by the person supported on the surface 22 in real time. With this approach, it is assumed that the zones 202, 204, 206, 208, and 210 are closed systems with no exchange of air between the zones 202, 204, 206, 208, and 210 and the outside environment during the measurement period. It is also assumed that there is negligible change of temperature during the measurement period such that the temperature can be assumed to be constant. This permits Boyle's law to be applied to calculate the work done in real time. With these assumptions, the only energy that can cross the boundary of the surface 22 as a closed system is heat or work. A measure of reversible boundary work is shown in Equation 3.

$$\text{Work}_{Boundary} = \int P dv \quad (3)$$

where P is absolute pressure in Pascals and V is volume. In a closed system with constant temperature, PV is constant. Therefore, at any two points in time, Equation 4 holds.

$$P_0 \cdot V_0 = P_1 \cdot V_1 \quad (4)$$

Since the volume can only be measured as an initial variable, Equation 4 is rearranged to Equation 5 below.

$$V_1 = \frac{P_0 \cdot V_0}{P_1} \quad (5)$$

Equation 5 is substituted into Equation 3 to calculate work according to Equation 6.

$$\text{Work}_{Boundary} = \int_{V_t}^{V_{t+n}} P(V) dV \quad (6)$$

Equation 6 can be reduced as shown below:

$$\text{Work}_{Boundary} = \int_{V_t}^{V_{t+n}} \frac{P_0 V_0}{V} dV \quad (7)$$

$$\text{Work}_{Boundary} = P_0 V_0 (\ln(V_{t+n}) - \ln(V_t)) \quad (8)$$

$$\text{Work}_{Boundary} = P_0 V_0 \cdot \ln\left(\frac{V_{t+n}}{V_t}\right) \quad (9)$$

substituting Equation 5 for $$\frac{V_{t+n}}{V_t},$$

$$\text{Work}_{Boundary} = P_0 V_0 \cdot \ln\left(\frac{P_t \cdot V_t}{V_t \cdot P_{t+n}}\right) \quad (10)$$

$$\text{Work}_{Boundary} = P_0 V_0 \cdot \ln\left(\frac{P_t}{P_{t+n}}\right) \quad (11)$$

Given that PV=mRT in an ideal gas and m is constant in a closed system, then the work performed from time t=1 to time t=2 can be expressed as the MobilityIndex according to Equation 12 below.

$$MobilityIndex_{Zone} = RT \cdot \ln\left(\frac{P_1}{P_2}\right) \quad (12)$$

where R for air is =0.287 (kJ/kg*K) and T is assumed to be a constant ambient temperature. When P2 is larger than P1, there is positive work into the zone and when P2 is less than P1, there is negative work, meaning the zone has worked on the person. The mobility index calculated from work may be converted to power by summing all of the members in a subset of an instant work array.

Each mobility index by zone may be averaged over a number of time windows to determine an average mobility index for a particular zone 202, 204, 206, 208, or 210. By utilizing the mobility index, a mobility score may be calculated for a person supported on the surface 22 by summing the mobility index for each of the zones 202, 204, 206, 208, and 210 to arrive at the composite score. The composite score is adjusted based on patient factors, bed configuration factors, and a scaling factor. Each of the factors are a numerical factor that is applied to the relative mobility index as shown in Equation 13 with each the product for each zone being summed to arrive at an overall mobility score.

$$MobilityScore = \sum_{Zones} (MobilityIndex_{Zone-x} \cdot Pf_{Zone-x} \cdot Bf_{Zone-x} \cdot Sf_{Zone-x}) \quad (13)$$

where Pf is the patient factor for the zone, Bf is the bed configuration factor for the zone, and Sf is the statistical scaling factor for the zone. Patient factors may include a patient's height, weight, body mass index, morphology, age, or other similar factors. The bed configuration factor may include weighting for the bed position or other factors that may be found empirically to impact patient mobility. The statistical scaling factoring may be a result of regression analysis or other statistical modeling to adjust for differences between the expected movement from a particular measurement and the actual movement that occurs as determined from empirical analysis.

It should be understood that each factor Pf, Bf, or Sf may vary for each zone. The response for a particular zone may be impacted differently. For example, the Pf may be smaller heavier patients than relatively lighter patients in a zone where a person's buttocks are located as movement and changes in pressure are more pronounced in those areas and the work done in that area can be discounted as compared to an area supporting only person's extremities.

A mobility score, such as the mobility score calculated using any one of the approaches described above, is used for various clinical analyses and as a predictor of the risk of injury to a patient. For example, the Braden Scale is a well-known approach for estimating the risk of the development of a pressure sores by a patient. The Braden Scale includes a mobility sub-scale that is assessed by caregivers in developing the overall score on the Braden Scale. The presently disclosed approaches to developing a mobility score may be normalized to match the Braden mobility sub-scale. The bed 10 may include software that utilizes data from several sources, including the mobility detection system disclosed herein, to calculate and output a score on the Braden Scale for a particular patient supported on the bed 10.

Figure 4:
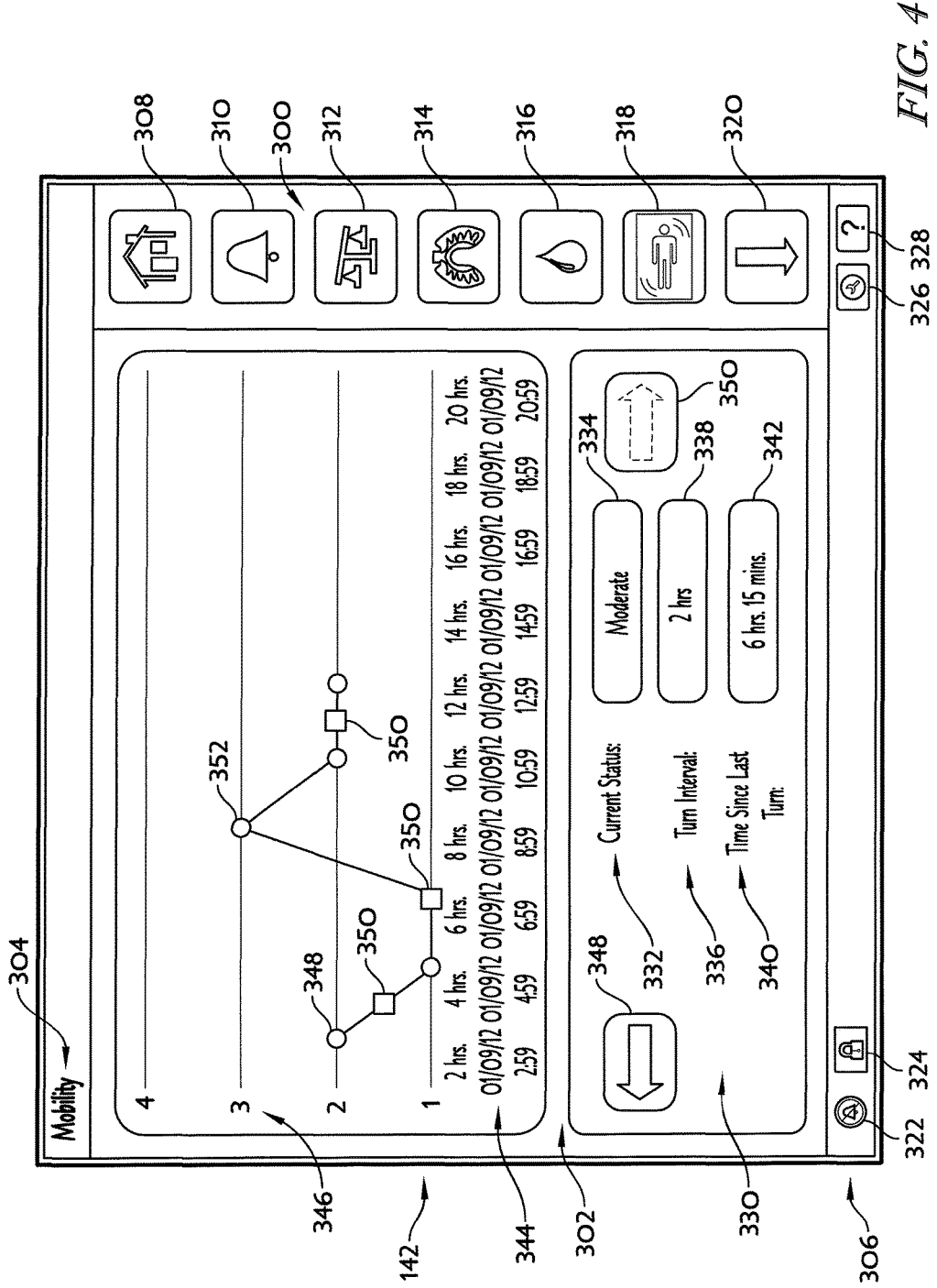
FIG. 4 is a screen shot of a first embodiment of a mobility screen that is displayed on a user interface of a patient support apparatus.

One approach to presenting a mobility score and mobility history for a person supported on the bed 10 is shown in FIG. 4. FIG. 4 presents an example of a touchscreen graphical display screen 142 that allows a user to visually review the mobility and mobility history of a person. In the illustrative embodiment of FIG. 4, the graphical display screen 142 includes a navigation bar 300 that includes a number of icons that allow a user to navigate to various functions which may be displayed on the graphical display screen 142 and which allow a user to modify operation of the bed 10. In FIG. 4, a first display area 302 presents charted data showing the mobility score for a person supported on the bed 10 at a given point in time. A second display area 330 allows a user to navigate through the charted data over time. A status bar 304 along the top of the display 142 provides an indication of what screen is being displayed. In some embodiments, the status bar 304 may also display information about the person supported on the bed 10, such as the patient's name, room number, the current time and date, or other information useful to a caregiver operating the bed 10.

A control bar 306 allows a user to activate an alarm silence icon 322 to silence alarms that may be active. In addition, a screen lock icon 324, when activated, allows a user to lock the display screen 142 so that no inputs will be processed without authorization. For example, a user may be prompted for a password, or the screen may remain locked until the system detects the presence of an authorization token, such as a radio frequency identification transmitter or a similar authorization device. In addition, an icon 326 may be activated by a user to call up a screen displaying maintenance function. An icon 328 may be activated to call up a screen displaying help functionality. In the illustrative embodiment, the control bar 306 is always available to a user regardless of the data or information displayed elsewhere on the graphical display screen 142.

Referring now to the navigation bar 300, a home screen icon 308 allows a user to immediately activate and jump to a home screen (not shown) from any screen display. Similarly, an alarm screen icon 310 will jump to an alarm screen (not shown) from any active screen. The illustrative embodiment of FIG. 4 also includes a scale screen icon 312, a therapy screen icon 314, a moisture screen icon 316, and a mobility screen icon 318. Each of the icons 312, 314, 316, and 318 allow a user to jump to the respective screens for the noted icons. An arrow icon 320 allows a user to move down the navigation bar 300 to display additional navigation icons.

The mobility screen of FIG. 4 includes a graph with a time line along the x-axis 344 and a mobility score along the y-axis 346. The control circuitry 98 is operable to utilize any of the techniques described above to determine a mobility score for the person supported on the bed 10. The mobility score at a given time is represented by the circular data points such as data points 348 and 352. The icons 350 each represent times of significant movement by the person on the bed 10. Additional information is provided in the second display area 330 including a current status 332 of the mobility of the person with the output 334 displaying a measure of the person's mobility. A turn interval indication 336 includes an output 338 that includes the expected turn interval for the person. The turn interval may be controlled by the therapy functionality available with the therapy screen icon 314, or it may be an indication of the protocol for the person showing how often a nurse or other caregiver should be turning the person as is known in the art. The display area 330 also has an actual turn interval indicator 340 with the time since the last turn displayed at 342. A left arrow icon 348 allows the user to move back in time to show the earlier data on the chart of the first display area 302. A right arrow icon 350 is shown to be inactive, but would be active if the there was data to be shown to the right of the current data.

Figure 5:
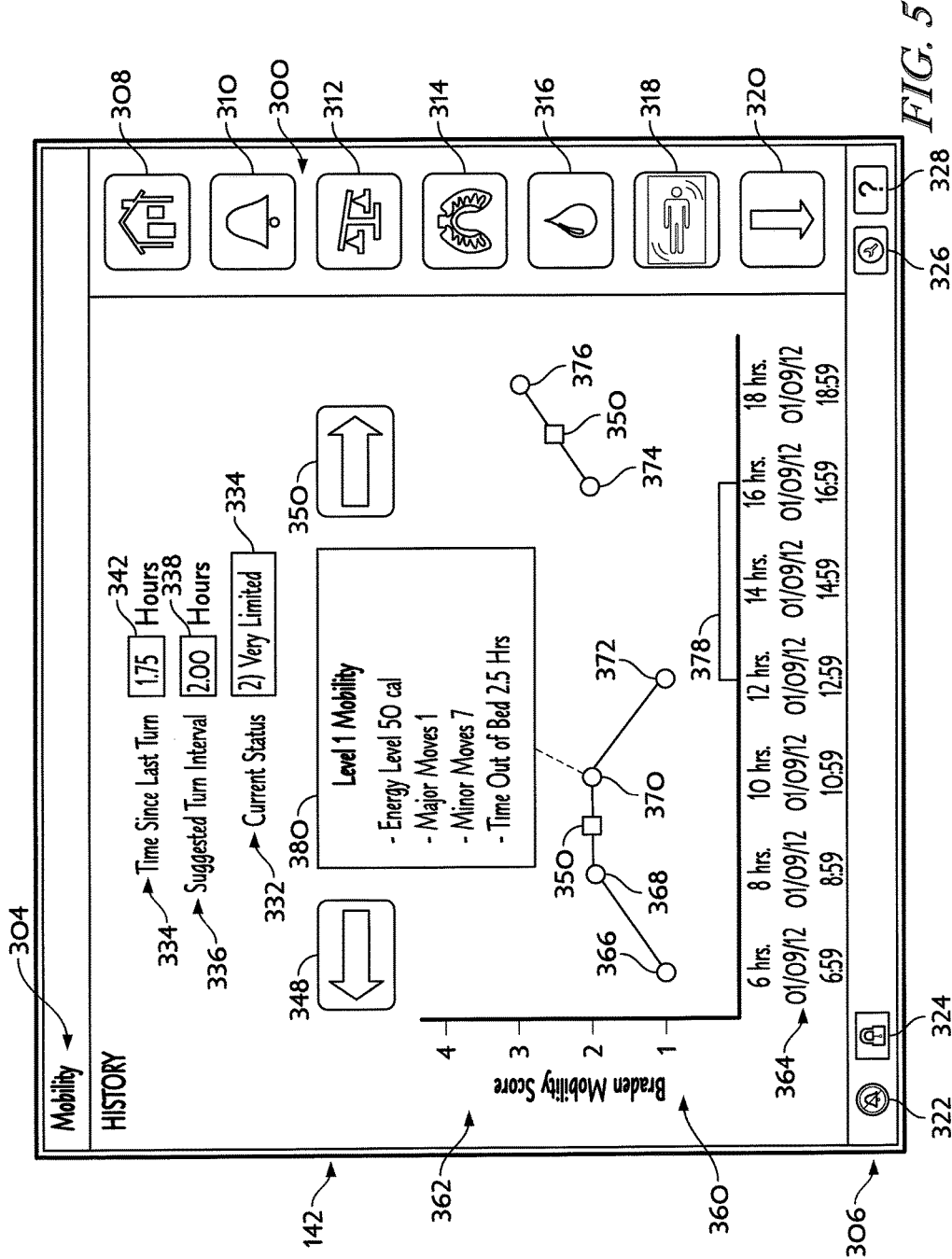
FIG. 5 is a screen shot of a second embodiment of a mobility screen that is displayed on a user interface of a patient support apparatus.

In another embodiment shown in FIG. 5, a display area 360 includes a chart similar to the chart of FIG. 4, but the chart of FIG. 5 is interactive so that a user can gather additional information from the chart. The Braden Mobility Score which is from the Braden mobility sub-scale is shown on the y-axis 362 with the time and data of each data point shown on the x-axis 364. The mobility score is shown with a number of data points 366, 368, 370, 372, 374, and 376. The major movement indicators 350 are also shown on the graph of FIG. 5. An out of bed indicator 378 gives an indication to the caregiver/user that the patient was out of bed for a period of time. As suggested in FIG. 5, a user can activate a data point to activate a pop up 380 that shows additional information. Illustratively in FIG. 5, a user has activated data point 370 to generate pop 380 which provides some additional information regarding the patient's mobility at that point in time. The remaining information displayed on the graphical display screen 142 of FIG. 5 is similar to that shown in FIG. 4 with like reference designators being used to indicate like information and icons.

Figure 6:
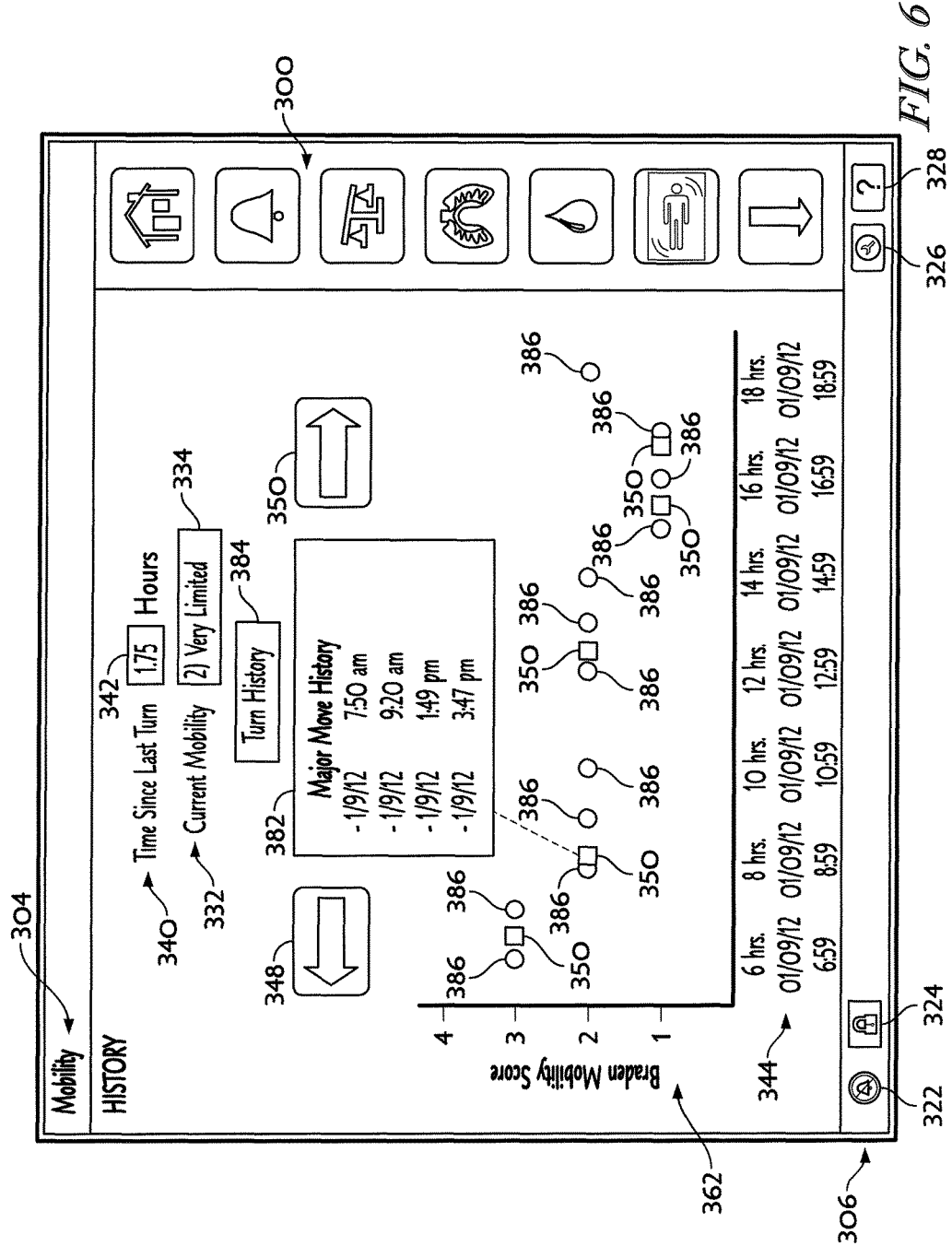
FIG. 6 is a screen shot of a third embodiment of a mobility screen that is displayed on a user interface of a patient support apparatus.

The illustrative embodiment of FIG. 6 show is similar to the embodiment of FIG. 5 with three differences. First, the embodiment of FIG. 6 includes a major move history pop up 382 that is shown when a user activates any of the major movement indicators 350. In addition, the suggested turn interval indictor 336 is omitted and an turn history icon 384 is available to allow a user to activate a pop up (not shown) to show the historical running list of when the person supported on the bed 10 has been turned, similar to the way the major move history is presented in the pop up 382. Finally, the data points 386 indicative of the Braden Mobility Score are not connected by lines.

Figure 7:
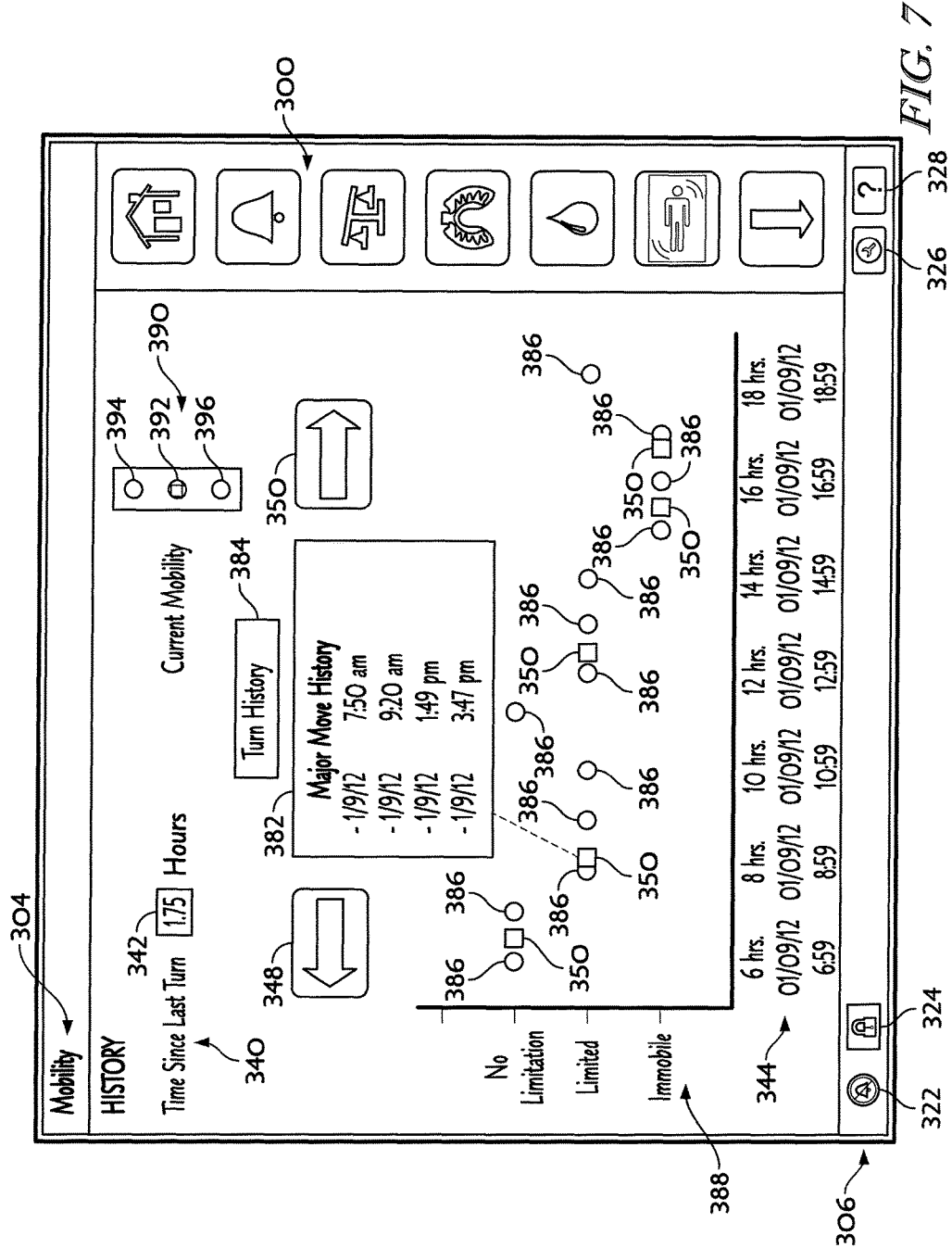
FIG. 7 is a screen shot of a fourth embodiment of a mobility screen that is displayed on a user interface of a patient support apparatus.

In the illustrative embodiment of FIG. 7, the relative mobility shown on the y-axis 388 does not correspond to the Braden mobility score, but is an alternate indicator of mobility graded between "immobile", "limited", and "no limitation." in addition, a graphical indicator 390 of the current mobility shows a limited indicator 392 illuminated. When the person has no limitation with regard to mobility, the graphical indicator 394 will be illuminated. If the person is immobile, the graphical indicator 396 will be illuminated.

Figure 8:
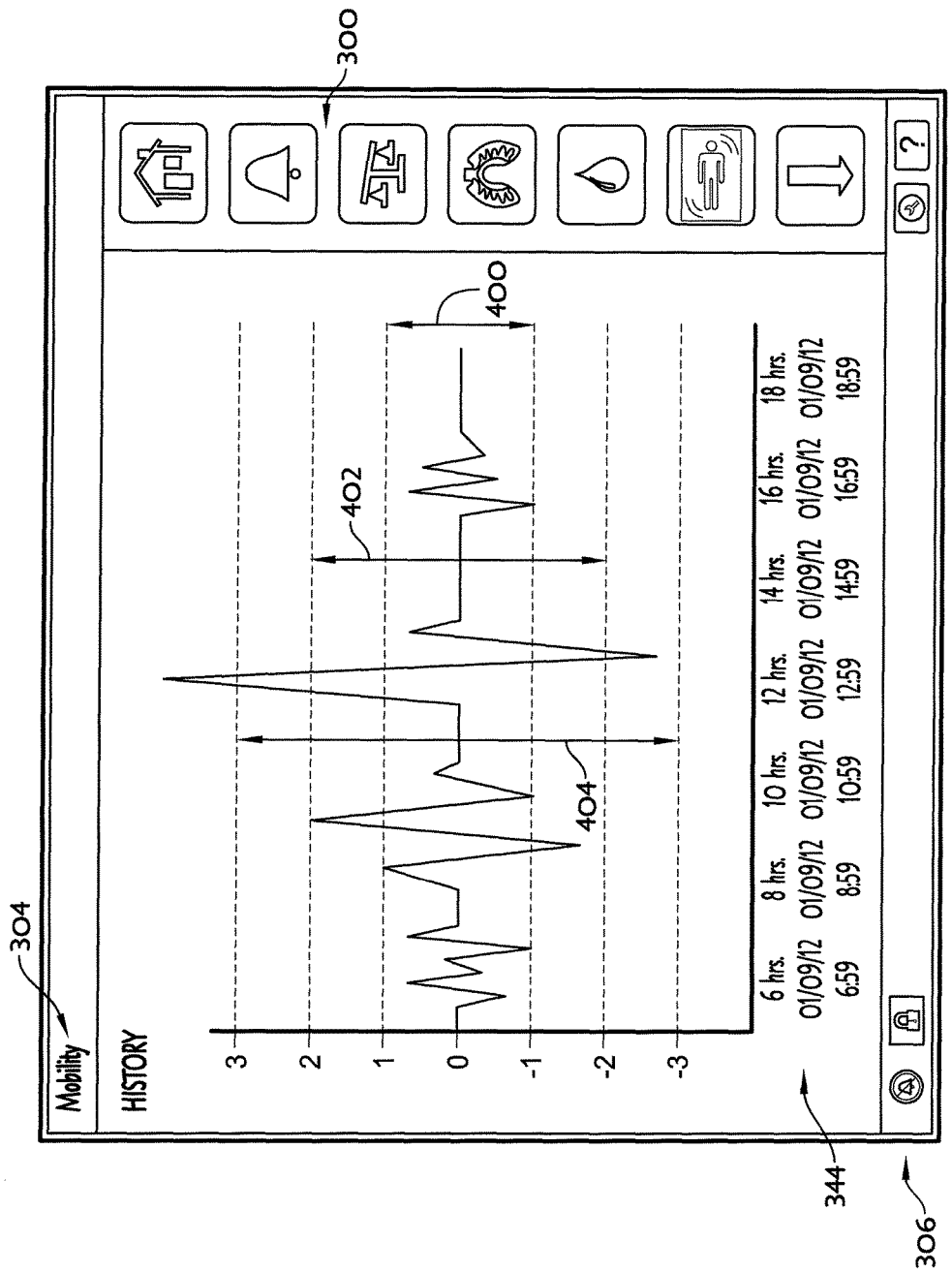
FIG. 8 is a screen shot of a second embodiment of a mobility screen that is displayed on a user interface of a patient support apparatus.

In still another approach shown in FIG. 8, the actual movement of the person on the bed 10 is shown graphically with the magnitude of movement providing a visual indication of the mobility of the person. A no mobility band 400 exists between mobility values of −1 to 1. A limited mobility band 402 exists between mobility values of −2 to 2 and a no limitation band 404 exists between mobility values of −3 to 3. In some embodiments, the graphical indicator 390 of the embodiment of FIG. 7 may be included in the embodiment of FIG. 8. When present, the graphical indicator 390 will be a mobility score based on a period of time with each of the instantaneous mobility values over a specified time period being considered in the calculation of the mobility score shown by the graphical indicator 390.

Although certain illustrative embodiments have been described in detail above, variations and modifications exist within the scope and spirit of this disclosure as described and as defined in the following claims.

The invention claimed is:

1. A patient support apparatus comprising
    a patient supporting surface including a number of bladders organized into a plurality of zones,
    a plurality of pressure sensors, each sensor in fluid communication with a respective zone and operable to measure a pressure in the respective zone,
    a user interface including a display and a number of user inputs, and
    a controller in communication with the pressure sensors to receive data signals indicative of the pressure in each of the zones, the controller including a processor and a non-transitory memory device, the memory device including instructions that, when executed by the processor, process the data signals from the pressure sensors to determine a mobility score of a patient supported on the patient supporting surface, wherein determining the mobility score for a patient includes determining a mobility index for each zone for a given time period by evaluating the coefficient of variation of pressure samples over time and summing the mobility index for each zone to determine the mobility score, and outputting an indication of the mobility score to a user.

2. The patient support apparatus of claim 1, wherein controller is in communication with the user interface and operable to cause the user interface to display the mobility score of the patient.

3. The patient support apparatus of claim 2, wherein the memory device further includes instructions that, when executed by the processor, cause the mobility score of the patient to be stored over time to create a data array.

4. The patient support apparatus of claim 3, wherein the memory device further includes instructions that, when executed by the processor, cause at least a portion of the array of the mobility score to be displayed as a graph.

5. The patient support apparatus of claim 1, wherein each of the mobility indices is modified by at least one predetermined factor.

6. The patient support apparatus of claim 5, wherein the at least one predetermined factor includes at least one of a patient factor, a bed factor, and a statistical scaling factor.

7. The patient support apparatus of claim 4, wherein the mobility score over time includes a number of data points.

8. The patient support apparatus of claim 7, wherein each of the data points may be activated to display additional information.

9. The patient support apparatus of claim 8, wherein the additional information includes a summary of data accumulated to the point in time corresponding with the data point.

10. The patient support apparatus of claim 9, wherein additional information regarding patient mobility is displayed on the display.

11. The patient support apparatus of claim 10, wherein the additional information includes a graphical indication of the time at which the patient moved relative to the patient supporting surface to change the patient's position relative to the patient support.

12. A patient support apparatus comprising
a patient supporting surface including a number of bladders organized into a plurality of zones,
a plurality of pressure sensors, each sensor in fluid communication with a respective zone and operable to measure a pressure in the respective zone,
a user interface including a display and a number of user inputs, and
a controller in communication with the pressure sensors to receive data signals indicative of the pressure in each of the zones, the controller including a processor and a non-transitory memory device, the memory device including instructions that, when executed by the processor, process the data signals from the pressure sensors to determine a mobility score of a patient supported on the patient supporting surface, and outputting an indication of the mobility score to a user,
wherein the mobility score of a patient supported on the patient supporting surface is determined by integrating the differences between an actual pressure measured and a pre-determined pressure over a predetermined period.

13. A patient support apparatus comprising
a patient supporting surface including a number of bladders organized into a plurality of zones,
a plurality of pressure sensors, each sensor in fluid communication with a respective zone and operable to measure a pressure in the respective zone,
a user interface including a display and a number of user inputs, and
a controller in communication with the pressure sensors to receive data signals indicative of the pressure in each of the zones, the controller including a processor and a non-transitory memory device, the memory device including instructions that, when executed by the processor, process the data signals from the pressure sensors to determine a mobility score of a patient supported on the patient supporting surface,
wherein the mobility score of a patient supported on the patient supporting surface is determined by determining a mobility index for each of the plurality of zones, wherein the mobility index for each zone is determined by calculating the work transferred from the patient supported on the zone of the patient supporting surface to the patient supporting surface, and summing each of the mobility indices to arrive at the mobility score, and outputting an indication of the mobility score to a user.

14. The patient support apparatus of claim 13, wherein each of the mobility indices is modified by at least one predetermined factor.

15. The patient support apparatus of claim 14, wherein the at least one predetermined factor includes at least one of a patient factor, a bed factor, and a statistical scaling factor.

16. The patient support apparatus of claim 15, wherein the mobility score over time includes a number of data points.

17. The patient support apparatus of claim 16, wherein each of the data points may be activated to display additional information.

18. The patient support apparatus of claim 17, wherein the additional information includes a summary of data accumulated to the point in time corresponding with the data point.

19. The patient support apparatus of claim 18, wherein additional information regarding patient mobility is displayed on the display.

20. The patient support apparatus of claim 19, wherein the additional information includes a graphical indication of the time at which the patient moved relative to the patient supporting surface to change the patient's position relative to the patient support.

* * * * *